United States Patent
Matta

(10) Patent No.: US 6,238,427 B1
(45) Date of Patent: May 29, 2001

(54) THERAPEUTIC HEAT TRANSFER PADS

(76) Inventor: John G. Matta, 1795 Bayhill Dr., Oldsmar, FL (US) 34677

(*) Notice: Subject to any disclaimer, the term of this patent is extended or adjusted under 35 U.S.C. 154(b) by 0 days.

(21) Appl. No.: 09/280,555

(22) Filed: Mar. 30, 1999

(51) Int. Cl.$^7$ ...................................................... A61F 7/00
(52) U.S. Cl. .......................................... 607/104; 607/108
(58) Field of Search ............................ 607/96, 104, 108, 607/109, 110, 111; 600/9

(56) References Cited

U.S. PATENT DOCUMENTS

| | | |
|---|---|---|
| D. 345,609 | 3/1994 | Mason et al. . |
| D. 348,106 | 6/1994 | Mason et al. . |
| D. 348,518 | 7/1994 | Mason et al. . |
| D. 348,733 | 7/1994 | Truelove . |
| D. 351,472 | 10/1994 | Mason et al. . |
| D. 352,781 | 11/1994 | Mason et al. . |
| D. 354,138 | 1/1995 | Kelly . |
| D. 354,139 | 1/1995 | Kelly . |
| D. 354,140 | 1/1995 | Kelly . |
| D. 357,747 | 4/1995 | Kelly . |
| D. 358,216 | 5/1995 | Dye . |
| D. 383,546 | 9/1997 | Amis et al. . |
| D. 383,547 | 9/1997 | Mason et al. . |
| D. 383,848 | 9/1997 | Mason et al. . |
| 1,847,619 | 3/1932 | Mascolo . |
| 3,500,832 | 3/1970 | Nunnery . |
| 3,674,034 | 7/1972 | Hardy . |
| 3,905,367 | 9/1975 | Dapcich . |
| 3,995,621 | 12/1976 | Fletcher et al. . |
| 4,108,146 | 8/1978 | Golden . |
| 4,353,359 | 10/1982 | Milbauer . |
| 4,566,455 | 1/1986 | Kramer . |
| 4,587,956 | 5/1986 | Griffin et al. . |
| 4,685,442 | 8/1987 | Cieslak . |
| 4,691,762 | 9/1987 | Elkins et al. . |
| 4,718,429 | 1/1988 | Smidt . |
| 4,745,922 | 5/1988 | Taylor . |
| 4,747,408 | 5/1988 | Chuan-Chih . |
| 4,753,242 | 6/1988 | Saggers . |
| 4,781,193 | 11/1988 | Pagden . |
| 4,800,867 | 1/1989 | Owens . |
| 4,844,072 | 7/1989 | French et al. . |
| 4,846,176 | 7/1989 | Golden . |
| 4,951,665 | 8/1990 | Schneider . |
| 4,962,761 | 10/1990 | Golden . |
| 5,072,875 | 12/1991 | Zacoi . |
| 5,080,089 | 1/1992 | Mason et al. . |
| 5,097,829 | 3/1992 | Quisenberry . |
| 5,174,285 | 12/1992 | Fontenot . |
| 5,190,032 | 3/1993 | Zacoi . |
| 5,230,335 | 7/1993 | Johnson, Jr. et al. . |
| 5,241,951 | 9/1993 | Mason et al. . |
| 5,266,778 | 11/1993 | Bailey . |

(List continued on next page.)

Primary Examiner—Lee Cohen
Assistant Examiner—R. Kearney

(57) ABSTRACT

A therapeutic heat transfer pad includes a pad assembly having two sheets of impervious material connected or bonded to one another by an edge seal or seam along perimeters thereof to form a fluid receiving cavity therebetween. The sheets are also connected or bonded to one another by a plurality of inner seals or seams located interiorly of the edge seal to define a plurality of interconnected fluid passages. A pair of fluid inlet tubes extend into the fluid receiving cavity from externally of the pad assembly for introducing a heat transfer fluid into the fluid receiving cavity. The inlet tubes enter the fluid receiving cavity at a common entry point or location and terminate within the fluid receiving cavity at open ends, respectively. The open ends of the inlet tubes are spaced from one another in the fluid receiving cavity and are adjacent and in communication with different ones of the fluid passages. An outlet tube extends from the fluid receiving cavity externally of the pad assembly and has an open end disposed in the fluid receiving cavity for removal of the heat transfer fluid therefrom.

17 Claims, 7 Drawing Sheets

U.S. PATENT DOCUMENTS

| | | |
|---|---|---|
| 5,269,369 | 12/1993 | Faghri . |
| 5,277,695 | 1/1994 | Johnson, Jr. et al. . |
| 5,314,455 | 5/1994 | Johnson, Jr. et al. . |
| 5,324,319 | 6/1994 | Mason et al. . |
| 5,330,519 | 7/1994 | Mason et al. . |
| 5,336,249 | 8/1994 | Mahawili . |
| 5,344,436 | 9/1994 | Fontenot et al. . |
| 5,363,663 | 11/1994 | Chen . |
| 5,383,919 | 1/1995 | Kelly et al. . |
| 5,389,061 | 2/1995 | Nor . |
| 5,411,541 | 5/1995 | Bell et al. . |
| 5,411,542 | 5/1995 | Jensen . |
| 5,417,720 | 5/1995 | Mason . |
| 5,426,925 | 6/1995 | Smargiassi . |
| 5,431,622 | 7/1995 | Pyrozyk et al. . |
| 5,433,741 | 7/1995 | Truglio . |
| 5,441,533 | 8/1995 | Johnson et al. . |
| 5,456,701 | 10/1995 | Stout . |
| 5,466,250 | 11/1995 | Johnson, Jr. et al. . |
| 5,470,353 | 11/1995 | Jensen . |
| 5,476,489 | 12/1995 | Koewler . |
| 5,486,207 | 1/1996 | Mahawili . |
| 5,496,357 | 3/1996 | Jensen et al. . |
| 5,496,358 | 3/1996 | Rosenwald . |
| 5,507,792 | 4/1996 | Mason et al. . |
| 5,584,086 | 12/1996 | VanWinkle et al. . |
| 5,591,220 | 1/1997 | Mahawili . |
| 5,603,728 | 2/1997 | Pachys . |
| 5,634,940 | 6/1997 | Panyard . |
| 5,643,336 | 7/1997 | Lopez-Claros . |
| 5,647,051 | 7/1997 | Neer . |
| 5,662,695 | 9/1997 | Mason et al. . |
| 5,683,438 | 11/1997 | Grahn . |
| 5,683,439 | 11/1997 | Jensen . |
| 5,720,773 | 2/1998 | Lopez-Claros . |
| 5,755,275 | 5/1998 | Rose et al. . |
| 5,755,755 | 5/1998 | Panyard . |
| 5,806,335 | 9/1998 | Herbert et al. . |
| 5,871,526 | 2/1999 | Gibbs et al. . |
| 5,888,185 | 3/1999 | Regan . |
| 5,984,855 | 11/1999 | DiNapoli . |
| 5,989,285 | 11/1999 | DeVilbiss et al. . |
| 6,086,609 | 7/2000 | Buckley . |
| B1 5,330,519 | 11/1998 | Mason et al. . |

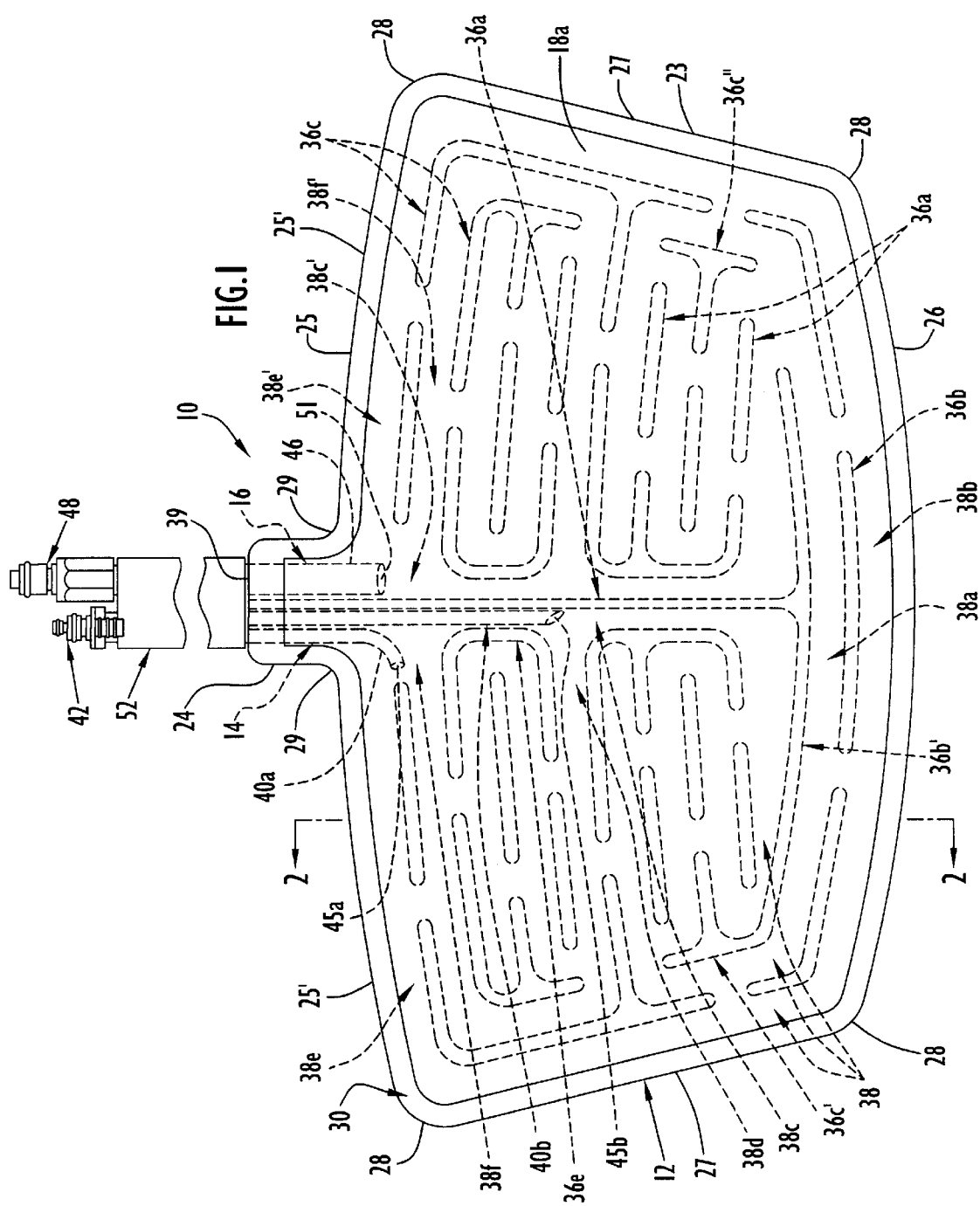

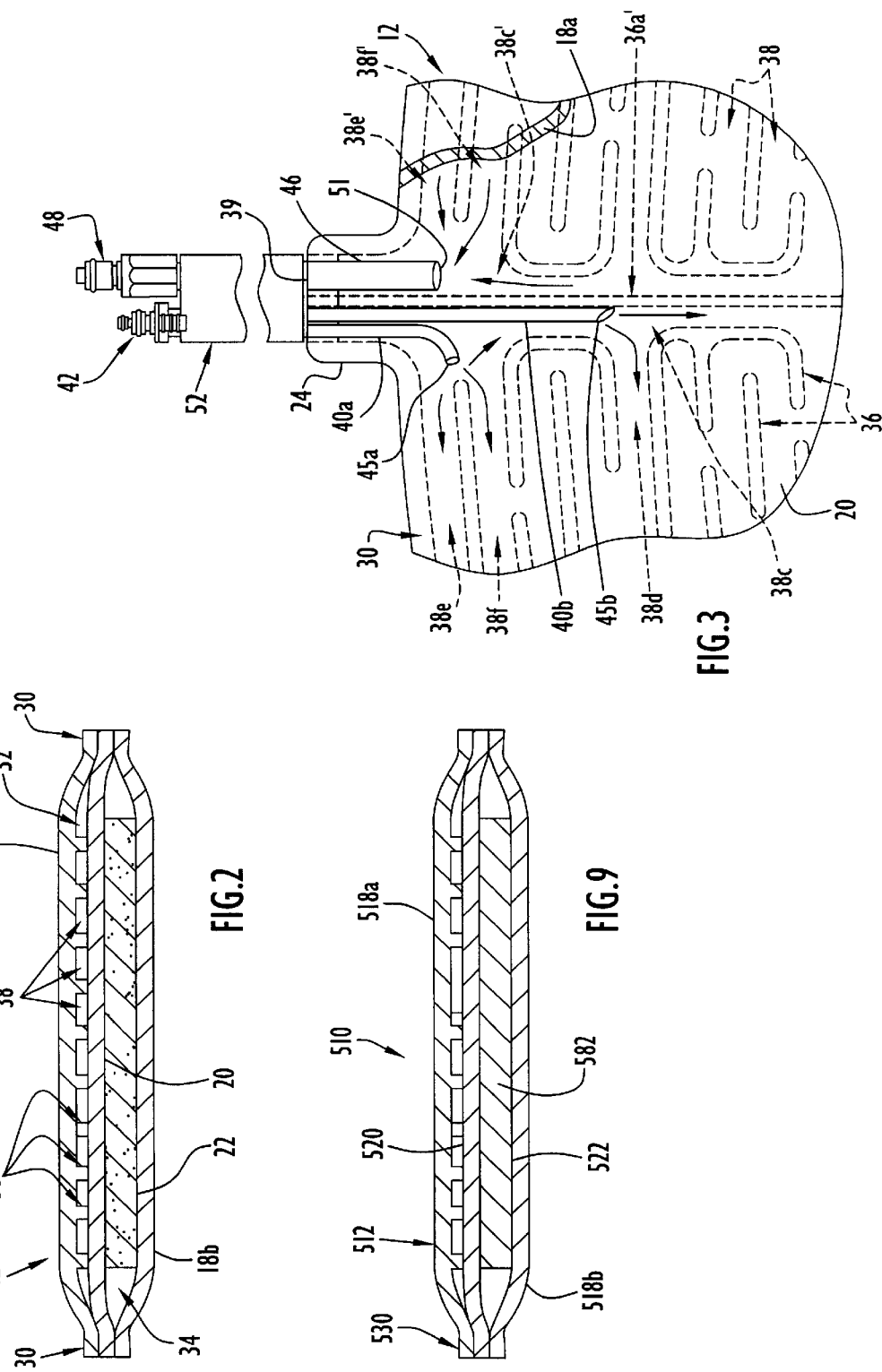

FIG. 8

THERAPEUTIC HEAT TRANSFER PADS

BACKGROUND OF THE INVENTION

1. Field of the Invention

The present invention relates to therapeutic treatment of human or animal bodily injuries, ailments or diseases by heating and/or cooling an affected body part or area and, more particularly, to heat transfer pads for being applied to an affected body part or area to obtain heating and/or cooling thereof via a heat transfer fluid supplied to the pads.

2. Brief Description of the Prior Art

It has become well known to treat human or animal bodily injuries, ailments and diseases by heating and/or cooling an affected body part or area. The application of heat and/or cold to an affected body part or area has been used to alleviate pain, accelerate healing, inhibit swelling or edema, reduce inflammation, reduce hematoma formation, improve flexibility and range of motion, decrease muscle spasm and restore strength. In particular, cold has been applied to an affected body part or area to slow down circulation and, therefore, the flow of blood to the affected body part or area, slow enzyme function and metabolic reactions, retard metabolism within tissue cells, contract blood vessels and block nerve impulses. The application of heat to an affected body part or area has been found to diminish pain impulses, increase collagen elasticity, accelerate cellular metabolism, dilate blood vessels, increase circulation and speed up the rate of enzymatic reactions. Injuries, ailments and diseases involving soft tissue, muscles, ligaments, tendons and/or joints have been effectively treated with heat and/or cold therapy. The application of heat and/or cold to a human or animal body has also been used to treat hypothermia and hyperthermia and to alter or maintain core body temperature.

In the equine area, heat and/or cold has been applied to body parts of horses for therapy and/or treatment of various conditions, such as sprains, strains and hock and knee injuries. Racehorses, in particular, must be maintained free from injury and/or soreness in order to be able to perform at an optimum level. Accordingly, heat and/or cold has been applied therapeutically to the legs of race horses, especially before and/or after a race.

Heat transfer pads defining an arrangement of fluid channels therein for continuously circulating a thermal transfer fluid within the pads have been used for localized heating and/or cooling of affected parts of the body as illustrated in U.S. Pat. No. 3,995,621 to Fletcher et al, U.S. Pat. Nos. 4,108,146, 4,846,176 and 4,962,761 to Golden, U.S. Pat. No. 4,691,762 to Elkins et al, U.S. Pat. No. 4,718,429 to Smidt, U.S. Pat. No. 4,745,922 to Taylor, U.S. Pat. No. 4,753,242 to Saggers, U.S. Pat. No. 4,844,072 to French et al, U.S. Pat. Nos. 5,072,875 and 5,190,032 to Zacoi, U.S. Pat. No. 5,174,285 to Fontenot, U.S. Pat. Nos. 5,241,951, 5,324,319, 5,330,519, B1 U.S. Pat. Nos. 5,330,519, 5,507, 792 and 5,662,695 to Mason et al, U.S. Pat. No. 5,344,436 to Fontenot et al, U.S. Pat. No. 5,372,608 to Johnson, U.S. Pat. No. 5,383,919 to Kelly et al, U.S. Pat. Nos. 5,411,542, 5,470,353 and 5,683,439 to Jensen, U.S. Pat. No. 5,417,720 to Mason, U.S. Pat. No. 5,456,701 to Stout, U.S. Pat. No. 5,486,207 to Mahawili, U.S. Pat. No. 5,496,357 to Jensen et al, U.S. Pat. No. 5,643,336 to Lopez-Claros, U.S. Pat. No. 5,806,335 to Herbert et al, U.S. Pat. No. Des. 357,747 to Kelly and U.S. Pat. No. Des. 383,546 to Amis et al.

A limb cooling apparatus for being wrapped around a limb of an animal, such as a race horse, is disclosed in U.S. Pat. No. 3,905,367 to Dapcich. The limb cooling apparatus includes an impermeable outer layer, a permeable inner layer and a flexible tube disposed between the inner and outer layers for supplying fluid therebetween. The permeable inner layer, which is placed in contact with the horse's limb, allows the fluid to pass therethrough to contact the horse's limb.

Prior heat transfer pads present various disadvantages and drawbacks, particularly for use on animals such as horses. In many prior heat transfer pads, the thermal transfer fluid is not distributed or circulated evenly throughout the pads thusly impairing the effectiveness of the pads. The fluid channels of many prior heat transfer pads may become blocked, closed, kinked or otherwise obstructed when the pads are folded or wrapped around a body part, resulting in undesired obstruction of fluid flow within the pads. The heat transfer pads typically include inlet and outlet tubes communicating with the interiors of the pads, and the inlet and outlet tubes of many prior heat transfer pads tend to undesirably kink or twist. The heat transfer pads are typically grasped and picked up by means of the inlet and/or outlet tubes; and, when so grasped and picked up, prior heat transfer pads undesirably sag or droop an excessive amount. Excessive sagging or drooping of the pads makes them difficult to use; and, when the pads sag or droop while fluid is disposed within the fluid channels, the fluid will likely not be distributed to all areas of the pads or will be distributed unevenly. Furthermore, many prior heat transfer pads are bulky and difficult to transport. When used on animals, such as horses, many prior heat transfer pads are not comfortable for the animal and/or require that normal movement of the animal be greatly restricted or that the animal be immobilized. Restriction of movement and/or immobilization of a horse are undesirable since it has been found that a horse will recover faster from injuries, diseases and ailments when free to move normally.

Magnetic therapy has also been used to treat bodily ailments, injuries and diseases in humans and animals. It is believed that application of a magnetic field to an ailing, injured or diseased body part or area influences biological processes so as to produce various beneficial effects. In particular, magnetic therapy is advocated for reducing pain and inflammation, relaxing muscle spasms, increasing joint mobility, speeding healing times, strengthening bodily tissues, stimulating blood circulation, improving oxygen consumption of cells and speeding up the exchange of oxygen and waste products in bodily tissues. The use of magnets in belts, bracelets, clothing and other items to be worn by the body have been proposed. As an example, wraps carrying a plurality of magnets have been proposed for placement on a horse's leg as illustrated by U.S. Pat. No. 5,389,061 to Nor and U.S. Pat. No. 4,587,956 to Griffen et al. In addition, magnets, such as those illustrated in U.S. Pat. No. 4,549,532 to Baermann and U.S. Pat. No. 4,489,711 to Latzke, have been secured on a horse's leg by tapes or bandages wrapped around the horse's leg. None of the devices previously proposed for magnetic therapy of a body part or area have incorporated a heat transfer fluid for simultaneous heat and/or cold thermal therapy of the body part or area.

Accordingly, the need exists for improved, therapeutic heat transfer pads having fluid passages or channels arranged therein so that fluid is supplied to all available areas of the pads. The need also exists for improved heat transfer pads that ensure proper fluid flow therein after the pads are applied to body parts or areas of humans or animals, particularly horses. The need further exists for improved heat transfer pads having fluid inlets designed to achieve better fluid distribution within the pads. In addition, there is a need for heat transfer pads wherein kinking and/or twisting of the inlet and/or outlet tubing is avoided. There is a further need for improved heat transfer pads particularly adapted for use on horses while being comfortable and without requiring significant restriction of movement or immobilization of the horses. There is also a need for therapeutic heat transfer pads capable of effecting heat and/or cold therapy as well as magnetic therapy.

SUMMARY OF THE INVENTION

Accordingly, it is a primary object of the present invention to overcome the aforementioned disadvantages of prior art heat transfer pads.

Another object of the present invention is to improve fluid distribution within a heat transfer pad.

A further object of the present invention is to ensure proper fluid flow within a heat transfer pad after it has been applied to a body part or area.

An additional object of the present invention is to arrange fluid passages or channels in a heat transfer pad so that fluid is distributed to all available areas of the pad.

It is also an object of the present invention to avoid obstruction of the fluid passages or channels of a heat transfer pad.

The present invention has as a further object to deter kinking and/or twisting of the inlet and/or outlet tubes of a heat transfer pad.

Yet another object of the present invention is to reduce sagging or drooping of a heat transfer pad when the heat transfer pad is picked up via its fluid inlet.

An additional object of the present invention is to provide support for a heat transfer pad when the heat transfer pad is picked up via its fluid inlet.

Still a further object of the present invention is to provide heat transfer pads in various configurations particularly suitable for use on the cannon, pastern, hock and fetlock areas of a horse's leg and on a horse's back.

Furthermore, it is an object of the present invention to provide heat transfer pads for heat and/or cold therapy of horses without requiring restriction of normal movement or immobilization of the horses.

The present invention has as an additional object to provide a heat transfer pad capable of effecting heat and/or cold therapy via a heat transfer fluid and capable of effecting magnetic therapy via one or more magnets carried by the pad.

Some of the advantages of the present invention are that the heat transfer pads are easily applied to various human or animal body parts or areas, the heat transfer pads are not excessively bulky or heavy, the heat transfer pads can be provided in various configurations in accordance with the configurations of body parts or areas to be treated, the heat transfer pads can be used for both heat and cold therapy, the heat transfer pads are comfortable for use on humans and animals, particularly horses, and magnetic therapy can be performed simultaneously with heat or cold therapy using a single device.

These and other objects, advantages and benefits are achieved with the present invention as generally characterized in a therapeutic heat transfer pad including a pad assembly, a fluid inlet and a fluid outlet. The pad assembly includes at least two sheets of flexible, impervious material disposed on top of one another and having perimeters continuously connected or secured to one another by a perimetrical edge seal or seam to define a fluid receiving cavity therebetween. The sheets are also secured or connected to one another by a plurality of inner seals or seams to define a plurality of interconnected fluid passages in the fluid receiving cavity. The fluid inlet includes two inlet tubes that pass between the sheets and enter the fluid receiving cavity from externally of the pad assembly. The inlet tubes enter the fluid receiving cavity at the same location and terminate at open ends disposed in the fluid receiving cavity. The open ends are disposed at different, spaced locations in the fluid receiving cavity and are in communication with different ones of the fluid passages to facilitate flow and distribution of a heat transfer fluid into the fluid passages via the inlet tubes. The fluid outlet includes an outlet tube that passes between the sheets and enters the fluid receiving cavity from externally of the pad assembly. The outlet tube terminates at an open end disposed in the fluid receiving cavity and through which the heat transfer fluid is removed therefrom. According to a preferred embodiment, the pad assembly includes an additional sheet of flexible, impervious material disposed on top of one of the aforesaid sheets and having a perimeter continuously connected or secured to the perimeter of the one sheet by the edge seal to define a space between the additional sheet and the one sheet. A panel, which may be made of soft, insulative material, is disposed in the space. The pad assembly can have various perimetrical or peripheral configurations in accordance with a body part or area to which the pad assembly is to be applied. When the therapeutic heat transfer pad is applied to a body part or area, the body part or area is treated thermally via thermal transfer by the heat transfer fluid within the pad assembly. The pad assembly may include one or more magnets disposed thereon for treating the body part or area magnetically; and, accordingly, a therapeutic heat transfer pad according to the present invention may be used to accomplish two different forms of therapy, i.e. thermal therapy and magnetic therapy.

Other objects and advantages of the present invention will become apparent from the following description of the preferred embodiments taken in conjunction with the accompanying drawings, wherein marked parts in each of the several figures are identified by the same reference characters.

BRIEF DESCRIPTION OF THE DRAWINGS

FIG. 1 is a broken, plan view of a therapeutic heat transfer pad according to the present invention.

FIG. 2 is a sectional view of the heat transfer pad taken along line 2—2 of FIG. 1.

FIG. 3 is a broken, fragmentary view, partly in section, of the heat transfer pad.

FIG. 8 is a broken, plan view of an additional modification of a therapeutic heat transfer pad according to the present invention.

FIG. 9 is a sectional view of yet another modification of a therapeutic heat transfer pad according to the present invention.

DESCRIPTION OF THE PREFERRED EMBODIMENTS

Figure 4:
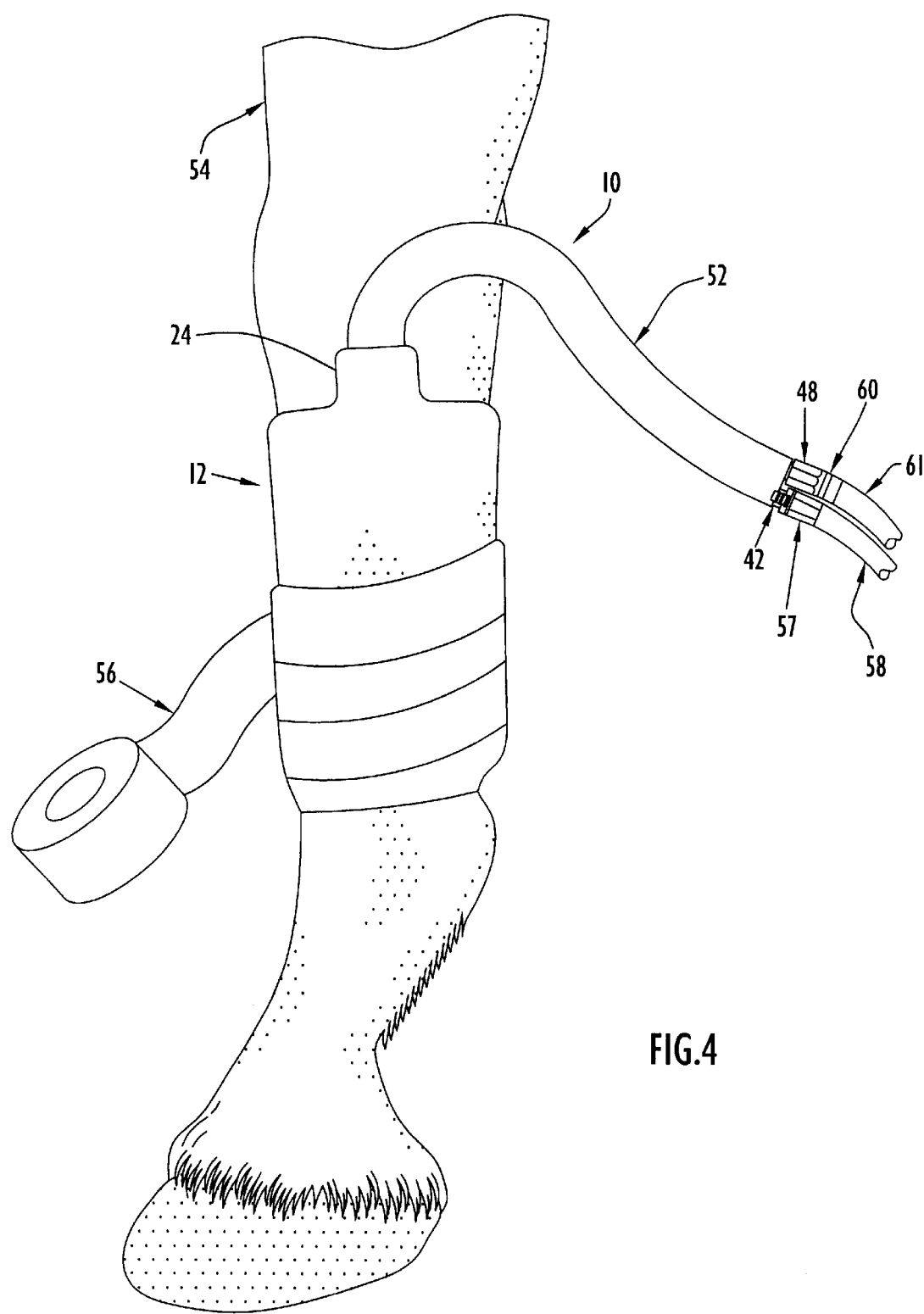
FIG. 4 is a broken, perspective view of the heat transfer pad being applied to an area of a horse's leg.

A therapeutic heat transfer pad 10 according to the present invention is illustrated in FIG. 1 and includes a pad assembly 12, a fluid inlet 14 communicating with the pad assembly 12 and a fluid outlet 16 communicating with the pad assembly 12. Pad assembly 12, as best shown in FIG. 2, includes outer sheets 18a and 18b, inner sheet 20 disposed between outer sheets 18a and 18b and a layer or panel 22 disposed between inner sheet 20 and outer sheet 18b. Outer sheets 18a and 18b and inner sheet 20 are each made of thin, flexible, flat or planar sheets of impervious or impermeable material capable of being flexed, bent or deformed to follow, conform to, surround or encircle the contour of a human or animal body part or area to which the pad assembly 12 is to be applied for treatment. Preferably, the outer sheets 18a and 18b and the inner sheet 20 are made of lightweight material, such as polyurethane, of uniform minimal thickness. In the case of pad assembly 12, sheets 18a, 18b and 20 are made of polyurethane film having a uniform thickness of approximately 7 mil to minimize bulk and weight and to facilitate bending, flexing or deforming of the pad assembly 12 when applied to a body part or area to be treated. The outer sheet 18b may be made of transparent material to permit visualization of fluid flow within the pad assembly as described further below.

The outer sheets 18a and 18b and the inner sheet 20 have the same planar size and shape so that the perimetrical or external peripheral edges thereof, respectively, are in alignment when the outer sheets 18a and 18b and the inner sheet 20 are disposed one on top of the other with the inner sheet 20 sandwiched between the outer sheets 18a and 18b. Since the sheets 18a, 18b and 20 all have the same planar size and configuration, the perimeter or external periphery of pad assembly 12 corresponds to or is the same as the individual external peripheries of sheets 18a, 18b and 20, respectively. The perimetrical or external peripheral edge of pad assembly 12 is, therefore, the same as the individual perimetrical or external peripheral edges, respectively, of sheets 18a, 18b and 20.

The perimeter or external periphery of pad assembly 12 defines or circumscribes an overall configuration or shape made up of a body portion 23 and a neck portion 24 extending from the body portion 23. The body portion 23 has a generally quadrilateral shape defined by upper and lower sides or edges 25 and 26, respectively, connected to one another by outer sides or edges 27 at curved or rounded outside corners 28. Upper side 25 is longer than lower side 26, which is longer than outer sides 27. Outer sides 27 are of the same length and extend angularly, at the same angle but in opposite directions, between sides 25 and 26. Neck portion 24, which is of uniform or substantially uniform width, protrudes outwardly beyond upper side 25 and is centrally located between outer sides 27 such that the overall configuration of pad assembly 12 is symmetrical about neck portion 24. Accordingly, upper side 25 is made up of upper side or edge segments 25' and the width of neck portion 24 disposed between side segments 25', the side segments 25' being connected to neck portion 24 at curved inside corners 29. Upper side segments 25' and lower side 26 have a gentle outward curvature while outer sides 27 are straight. The configuration of body portion 23 is particularly suited for use on the cannon/pastern area of a horse's leg.

The panel 22 has the same overall configuration or shape as the sheets 18a, 18b and 20 without neck portion 24, but is smaller in perimetrical or external peripheral size than the sheets 18a, 18b and 20. Therefore, the panel 22 has a perimeter or external periphery disposed within or inside of the perimeter or external periphery of the pad assembly 12 when the panel 22 is disposed between outer sheet 18b and inner sheet 20. In the case of pad assembly 12, panel 22 has a perimeter or external periphery defining or circumscribing a generally quadrilateral configuration or shape corresponding to but smaller than the quadrilateral configuration or shape of sheets 18a, 18b and 20 without neck portion 24. When panel 22 is disposed between outer sheet 18b and inner sheet 20 with the panel 22 centered relative to the perimeters of sheets 18a, 18b and 20, external peripheral or perimetrical border portions of the outer sheets 18a and 18b and the inner sheet 20, respectively, circumscribe or surround the perimetrical or external peripheral edge of panel 22. The panel 22 is preferably made of a thin, planar or flat, layer or sheet of soft, flexible material, such as foam, that is capable of flexing, bending or deforming with sheets 18a, 18b and 20 when the pad assembly 12 is applied to a body part or area to be treated. In the case of pad assembly 12, panel 22 is made of polyethylene foam having a thickness of ¹⁄₁₆ inch. Preferably, panel 22 is made of soft material to serve as padding and is preferably made of insulative material to reduce heat transfer to and from a thermal transfer fluid within the pad assembly as explained below.

As shown in FIGS. 1 and 2, sheets 18a, 18b and 20 are secured to one another at a perimetrical or external peripheral edge seal or seam 30 extending continuously along their perimetrical or external peripheral edges, respectively. The sheets 18a, 18b and 20 may be secured to one another in various ways including heat sealing, heat fusing, solvent sealing, adhesives or any other means compatible with the material or materials from which the sheets are made. The perimetrical or external peripheral edge of panel 22 is disposed within or inside of the edge seal 30 without being secured to sheets 18a, 18b or 20. With the sheets 18a, 18b and 20 secured to one another along edge seal 30, a first or fluid receiving cavity or space 32 is formed between outer sheet 18a and inner sheet 20, and a second cavity or space 34 is formed between inner sheet 20 and outer sheet 18b. The second cavity 34 has the layer 22 captured therein between inner sheet 20 and outer sheet 18b and does not communicate fluidically with cavity 32.

The outer sheet 18a and the inner sheet 20 are also secured to one another along inner seals or seams 36 interiorly of edge seal 30 to define a plurality of interconnected fluid passages or channels 38 in cavity 32. The outer sheet 18a and the inner sheet 20 may be secured to one another along inner seals 36 in the same manner as that used to secure sheets 18a, 18b and 20 along edge seal 30. A preferred arrangement for inner seals 36 and fluid passages 38 is shown in dotted lines in FIG. 1, such an arrangement serving to facilitate fluid flow and distribution to all available areas of the fluid receiving cavity 32 and to deter obstruction of fluid flow when the pad assembly 12 is applied to a body part or area.

As shown in FIG. 1, inner seals 36 include a plurality of straight inner seals 36a, a plurality of curved inner seals 36b and a plurality of angular inner seals 36c. One of the straight inner seals, i.e. inner seal 36a', bisects the neck portion 24 longitudinally and extends into the body portion 23, the inner seal 36a' being centrally disposed in the body portion 23. The inner seal 36a' extends from an outer edge or end 39 of neck portion 24 to terminate in the body portion 23 at an end spaced inwardly from side 26. The remaining inner seals 36, none of which touches the edge seal 30, are arranged symmetrically around inner seal 36a' except for one of the curved inner seals, i.e. inner seal 36b', which is joined to or continuous with the end of inner seal 36a'. Inner seal 36b' extends transversely to inner seal 36a' and parallel to lower side 26. Inner seal 36b' has an end joined to or continuous with one of the angular inner seals, i.e. angular inner seal 36c', disposed on one side of inner seal 36a' and an end terminating on an opposite side of inner seal 36a'. The end of seal 36b' that terminates on the opposite side of seal 36a' is spaced from and not connected to the inner seal 36c'' disposed on the opposite side of seal 36a' and corresponding to the inner seal 36c'. The angular inner seals 36c' and 36c'' have a T-shaped configuration. Fluid supplied to cavity 32 flows from the one side of seal 36a' to the opposite side thereof via fluid passages 38a and 38b disposed between inner seal 36b' and edge seal 30 along lower side 26, the passages 38a and 38b being parallel to inner seal 36b' and side 26. Various shapes of angular inner seals are provided in pad assembly 12 including T shaped, C shaped, F shaped and E shaped angular inner seals. Some of the inner seals follow the bend, angle or curve of outside corners 28, some are parallel to sides 26 and 27 and some extend in the same direction as side 25.

The fluid inlet 14 includes two flexible inlet tubes 40a and 40b and an inlet coupling 42 for releasably coupling inlet tubes 40a and 40b to a source of fluid (not shown). Typically, the inlet coupling is coupled or connected to a fluid supply conduit (shown in FIG. 4), which communicates with the fluid source to supply fluid to inlet tubes 40a and 40b and, therefore, cavity 32. As shown in FIGS. 1 and 3, inlet tubes 40a and 40b are disposed between outer sheet 18a and inner sheet 20 and extend into cavity 32 from externally of pad assembly 12, the inlet tubes 40a and 40b entering the fluid receiving cavity 32 at the same or a common entry point or location. The common entry point or location for inlet tubes 40a and 40b is at neck portion 24, through which the inlet tubes enter the pad assembly via an outer edge or end 39 of neck portion 24. The inlet tubes extend longitudinally through neck portion 24 into the body portion 23 on the one side of seal 36a'. The inlet tubes 40a and 40b each have a first length portion disposed within pad assembly 12 and a second length portion extending externally of pad assembly 12. The inlet tubes are disposed closely side by side or alongside one another at the common entry point or location. The inlet tubes 40a and 40b terminate at open ends 45a and 45b, respectively, disposed in cavity 32 internally or interiorly of edge seal 30, the open ends 45a and 45b being disposed in the body portion 23. Opposite, open ends of inlet tubes 40a and 40b, respectively, are secured to coupling 42, which is disposed externally of pad assembly 12, and are in fluid communication with a passage extending longitudinally through the coupling 42. The inlet tubes 40a and 40b are secured to pad assembly 12 and are held in place along the outer edge 39 by edge seal 30 and, in particular, by a segment or portion of edge seal 30 along the outer edge 39, such edge seal portion extending transverse to the inlet tubes. The inlet tubes 40a and 40b are preferably made of transparent, flexible tubing, such as polyurethane, polyethylene or other flexible plastic tubing having an inside diameter of 1/8 inch and an outside diameter of 1/4 inch. Inlet coupling 42 can be designed in various ways for being coupled or connected to the source of fluid. In the case of heat transfer pad 10, the inlet coupling 42 is a male coupling for being coupled or connected to a female coupling of a fluid supply conduit communicating with the fluid source. The second length portions of inlet tubes 40a and 40b can be any desired length to facilitate connection or coupling of the inlet tubes to the fluid supply conduit.

One of the inlet tubes is longer than the other to extend into the cavity 32 and, in particular, the body portion 23, a greater distance than the other. Accordingly, the open ends of the inlet tubes are disposed in cavity 32 at different, spaced locations. As shown in FIGS. 1 and 3, inlet tube 40b, which is disposed next to or alongside inner seal 36a', is longer than inlet tube 40a. The first length portion of inlet tube 40b follows a straight or substantially straight path and is disposed parallel or substantially parallel to inner seal 36a', the inlet tube 40b extending within a fluid passage 38c that extends along the inner seal 36a'. Part of fluid passage 38c is defined on one side by inner seal 36a' and on the other side by an inner seal 36c. There may be a small gap between the inlet tube 40b and seals 36a' and 36e allowing fluid to flow between the inlet tube 40b and seals 36a' and 36e. The open end 45b of inlet tube 40b is disposed in cavity 32 at a location where the fluid passage 38c intersects or meets a fluid passage 38d. Accordingly, the open end 45b communicates directly with more than one fluid passage and, in particular, two different fluid passages. The fluid passage 38d is disposed transverse to fluid passage 38c, the fluid passage 38c extending vertically or up and down and the fluid passage 38d extending horizontally or side to side.

The first length portion of inlet tube 40a follows a partly straight path and a partly curved path. The first length portion of inlet tube 40a includes a straight or substantially straight length segment extending along neck portion 24 into cavity 32 and merging with a curved length segment. The straight or substantially straight length segment of tube 40a is disposed next to or alongside tube 40b parallel therewith, with little or no gap between tube 40b and the straight or substantially straight length segment of tube 40a. Tube 40b and the straight or substantially straight length segment of tube 40a are held or constrained laterally between inner seal 36a' and a portion or segment of edge seal 30 extending along a side of neck portion 24 disposed on the one side of seal 36a'. The tubes 40a and 40b are prevented from moving longitudinally by the segment or portion of edge seal 30 along upper edge 39. The curved length segment of tube 40a curves or bends laterally from the straight or substantially straight length segment in the direction of the side 27 disposed on the one side of inner seal 36a'.

The open end 45a of inlet tube 40a terminates in cavity 32 at a location where fluid passage 38c meets or intersects fluid passages 38e and 38f. The fluid passages 38e and 38f, which extend horizontally or side to side, extend transversely to fluid passage 38c. The open end 45a thusly communicates directly with three different fluid passages. The end 45b of tube 40b is disposed in cavity 32 further inwardly or interiorly than end 45a of tube 40a. Except for fluid passage 38c, the ends 45a and 45b communicate directly with different fluid passages. Where the ends 45a and 45b communicate directly with the same fluid passage, i.e. fluid passage 38c, the ends communicate with such same fluid passage at different, spaced locations. The open ends 45a and 45b may be angled or beveled to face the fluid passages with which they are in direct communication. The use of double inlet tubes for fluid inlet 14 and the extension of the inlet tubes into the cavity 32 and, in particular, the body portion 23, results in better fluid flow and distribution within the cavity 32 to ensure that all available areas of the cavity 32 are supplied or filled with fluid, even when the pad assembly 12 is flexed, bent or otherwise deformed for application to a body part or area to be treated. In particular, fluid entering cavity 32 via the open ends 45a and 45b of inlet tubes 40a and 40b, respectively, enters the cavity 32 at different, separate locations spaced from one another in cavity 32. In addition, fluid entering the cavity 32 from either of the open ends 45a or 45b, is distributed directly to more than one fluid passage as shown by the arrows in FIG. 3 on the one side of seal 36a'. In this manner, fluid entering cavity 32 is more widely dispersed upon entry therein and is distributed more rapidly to all of the fluid passages 38.

The fluid outlet 16 includes a flexible outlet tube 46 and an outlet coupling 48 for releasably coupling outlet tube 46 to a fluid receiver (not shown). Typically, the outlet coupling is coupled or connected to a fluid removal conduit (shown in FIG. 4), communicating with the fluid receiver to remove or withdraw fluid from cavity 32. As shown in FIGS. 1 and 3, outlet tube 46 is disposed between outer sheet 18a and inner sheet 20 and extends into cavity 32 from externally of pad assembly 12. The outlet tube 46 enters pad assembly 12 at the outer edge or end 39 of neck portion 24 and extends longitudinally through neck portion 24 into the body portion 23 on the opposite side of seal 36a'. Accordingly, in the case of pad 10, the outlet tube enters the pad assembly at the same entry point or location as the inlet tubes. The outlet tube 46 has a first length portion disposed within pad assembly 12 and a second length portion extending externally of pad assembly. The outlet tube 46 terminates at an open end 51 disposed in cavity 32. An opposite, open end of outlet tube 46 is secured to coupling 48, which is disposed externally of pad assembly 12 and is in fluid communication with a passage extending longitudinally through the coupling 48. The outlet tube 46 is secured to pad assembly 12 and is held in place at the outer edge 39 of neck portion 24 by the segment or portion of edge seal 30 along the outer edge 39. The outlet tube 46 is preferably made of transparent, flexible tubing, such as polyurethane, polyethylene or other flexible plastic tubing, having an inside diameter of ¼ inch and an outside diameter of ⅜ inch. Outlet coupling 48 can be designed in various ways for being coupled or connected to the fluid receiver. In the case of heat transfer pad 10, the outlet coupling 48 is a female coupling for being coupled or connected to a male coupling of a fluid removal conduit. The second length portion of outlet tube 46 preferably is of the same length as the second length portions of inlet tubes 40a and 40b.

The first length portion of outlet tube 46 is disposed next to or alongside the inner seal 36a' on the opposite side thereof, the first length portion of outlet tube 46 being held or constrained laterally between seal 36a' and a portion or segment of edge seal 30 extending along a side of neck portion 24 disposed on the opposite side of seal 36a'. The outlet tube 46 is prevented from moving longitudinally by the segment or portion of seal 30 along upper edge 39. The open end 51 of the outlet tube 46 is disposed in cavity 32, on the opposite side of seal 36a', at a location where fluid passage 38c' meets or intersects fluid passages 38e' and 38f' corresponding to fluid passages 38e and 38f on the one side of seal 36a'. Accordingly, the open end 51 communicates directly with three different fluid passages, i.e. fluid passages 38c', 38e' and 38f'. The open end 51 is not beveled or angled; however, the open end 51 may be beveled or angled to face the fluid passages with which it is in direct communication. Fluid in the cavity 32 is continuously removed or withdrawn therefrom through the outlet tube 46, as shown in FIG. 3 by arrows on the opposite side of seal 36a', with the location of the open end 51 in direct communication with more than one fluid passage facilitating fluid withdrawal for enhanced, continuous circulation of fluid within the pad assembly 12.

A sheath 52, preferably made of a flexible, compressible or deformable, insulative material, such as polyurethane foam, is disposed over the second length portions of the inlet tubes 40a and 40b and the outlet tube 46. The sheath 52 is hollow or tubular and has a lumen or passage entirely therethrough for receiving the inlet and outlet tubes therein. Preferably, the lumen of the sheath 52 has a cross-sectional size to snugly receive the inlet and outlet tubes therein, the inlet and outlet tubes being arranged in the lumen of the sheath in side by side relation. Depending on the material utilized for sheath 52, the sheath lumen may stretch or expand to accommodate the inlet and outlet tubes and/or may compressively engage the inlet and outlet tubes. The sheath 52 extends from the outer edge 39 of neck portion 24 to the couplings 42 and 48. Sheath 52 provides insulation for the inlet and outlet tubes to minimize the transfer of heat to and from the fluid carried by the tubes. Additionally, the sheath 52 inhibits twisting and/or kinking of the inlet and outlet tubes.

In order to use the therapeutic heat transfer pad 10 to treat a body part or area, the heat transfer pad 10 is typically picked up by grasping the fluid inlet 14 and the fluid outlet 16 and, in particular, by grasping the sheath 52. When held horizontally via the sheath 52, the pad assembly 12 is supported horizontally due to extension of the inlet tubes 40a and 40b and the outlet tube 46 into the cavity 32. The pad assembly 12 does not bend or sag excessively such that the fluid passages and the open ends of the inlet and outlet tubes are not blocked or obstructed. The pad assembly 12 is positioned over a body part or area to be treated, and the manner in which the pad assembly 12 is placed on the body part or area to be treated is determined by the configuration of the pad assembly and the contour of the body part or area to be treated. For example, the pad assembly may merely rest upon a body part or area, such as the back, to be supported by the body part or area, or the pad assembly may be wrapped around a body part or area, such as a limb, to encircle or surround the body part or area.

FIG. 4 illustrates the pad assembly 12 wrapped around an area of a horse's leg 54. As shown in FIG. 4, the pad assembly 12 is positioned around the horse's leg 54 with the longer, upper edge or side 25 disposed around the wider, upper part of the horse's leg and the shorter, lower edge or side 26 disposed around the narrower, lower part of the horse's leg. The neck portion 24 is vertically or substantially in line with the horse's leg 54 such that the inlet tubes 40a and 40b extend or are directed downwardly, such an arrangement taking advantage of gravity to facilitate the flow of heat transfer fluid into the cavity 32 via the fluid inlet 14. The outer edges or sides 27 of the pad assembly 12 will typically overlap one another thusly ensuring that the pad assembly 12 encircles or surrounds the entire circumference of the area of the horse's leg to be treated.

The pad assembly 12 is secured in position around the horse's leg 54 by a length of tape 56, which is wrapped around the horse's leg over the pad assembly 12. FIG. 4 shows the tape 56 partially applied over the pad assembly 12 in that a portion of pad assembly 12 is still uncovered or unwrapped by tape 56. Various conventional tapes used for taping, wrapping or bandaging body parts or areas may be used for tape 56 including resilient or stretchable tapes, wraps or bandages, which may be self-securing or non-self-securing. Preferably, the tape 56 is wrapped around the entire pad assembly 12. Once wrapping of tape 56 around the pad assembly 12 has been completed, the tape 56 is secured in place due to being self-securing or, where the tape 56 is not self-securing, with the use of clips or other securing elements. When thusly wrapped around the pad assembly 12, the tape 56 secures the pad assembly in position on the body part or area and provides an insulative function to minimize the transfer of heat to and from the pad assembly 12.

The inlet coupling 42 is coupled or connected with a female coupling 57 of a fluid supply conduit 58 which, in turn, is connected to a source or supply (not shown) of heat or thermal transfer fluid, such as water. The heat transfer fluid will typically be pumped through the fluid supply conduit 58 and into the inlet tubes 40a and 40b, the heat transfer fluid flowing through the passage of the inlet coupling 42 into the inlet tubes. Accordingly, the heat transfer fluid will be discharged, as assisted by gravity, from the open ends 45a and 45b of inlet tubes 40a and 40b, respectively, into cavity 32. The heat transfer fluid may be introduced in cavity 32 at a desired temperature depending on whether heat or cold therapy is to be performed. The source or supply of the heat transfer fluid may include a heating and/or cooling system for heating and/or cooling the heat transfer fluid as well as a temperature selector, to which the heating and/or cooling system is responsive, for introducing fluid at a desired temperature into cavity 32. Prior to introducing heat transfer fluid into cavity 32, the outlet coupling 48 is connected or coupled with a male coupling 60 of a fluid removal conduit 61 which, in turn, is connected with a fluid receiver (not shown). It should be appreciated that the source or supply of the heat transfer fluid may incorporate the fluid receiver therein to form a closed system for continuously circulating the heat transfer fluid at a desired temperature through the pad assembly 12.

As the heat transfer fluid is discharged from the open ends 45a and 45b of the inlet tubes 40a and 40b, respectively, into the cavity 32, the fluid flows into all of the fluid passages 38 such that all available areas of the cavity 32 are filled or supplied with the heat transfer fluid. Distribution of the heat transfer fluid throughout the cavity 32 is enhanced due to extension of the inlet tubes 40a and 40b into the cavity 32 and, in particular, into the body portion 23, as well as extension of the inlet tube 40b into the cavity 32 beyond the inlet tube 40a. As shown by the arrows on the one side of inner seal 36a' in FIG. 3, the heat transfer fluid enters the cavity 32 at two different locations, which are disposed at different depths within the cavity 32. In addition, the heat transfer fluid is discharged from the open ends 45a and 45b of the inlet tubes into different ones of the fluid passages with each open end discharging fluid into more than one fluid passage. In the case of heat transfer pad 10, fluid is discharged from open end 45a into fluid passages 38c, 38e and 38f while fluid is discharged from open end 45b into fluid passages 38c and 38d. Once the cavity 32 is completely filled with the heat transfer fluid, continued introduction of the heat transfer fluid into the cavity 32 causes the heat transfer fluid to exit the cavity 32 via the outlet tube 46 for removal therefrom. Of course, the outlet tube 46 could be connected with a source of suction to actively remove fluid from cavity 32. The fluid discharged from outlet tube 46 flows through the fluid removal conduit 61 to the fluid receiver. In a closed system, the fluid collected by the fluid receiver is heated or cooled to the selected desired temperature and is reintroduced into the cavity 32. The heat transfer fluid may be continuously introduced into the cavity 32 and may be continuously discharged from the cavity 32 such that the heat transfer fluid is continuously circulated through the pad assembly 12. The panel 22 and the tape 56 both serve to reduce heat transfer to and from the fluid circulating within the pad assembly 12. The body part or area to which the pad is applied will be treated via thermal heat transfer of the heat transfer fluid within the pad assembly. While undergoing heat or cold therapy utilizing the heat transfer pad 10, the horse need not be immobilized but, rather, may engage in substantially normal behavior and movement. Once thermal therapy has been effected for a desired length of time, the couplings 42 and 50 are disconnected from the couplings 57 and 60, respectively. The tape 56 and the heat transfer pad 10 may be removed from the horse's leg, or the tape 56 and heat transfer pad 10 may remain in place to allow heat or cold therapy to be performed again at a later time. It should be appreciated that a separate therapeutic heat transfer pad can be used on more than one part or area of a body for treatment of multiple body parts or areas at the same time. For example, separate heat transfer pads 10 can be used on each of a horse's legs to be treated.

Figure 5:
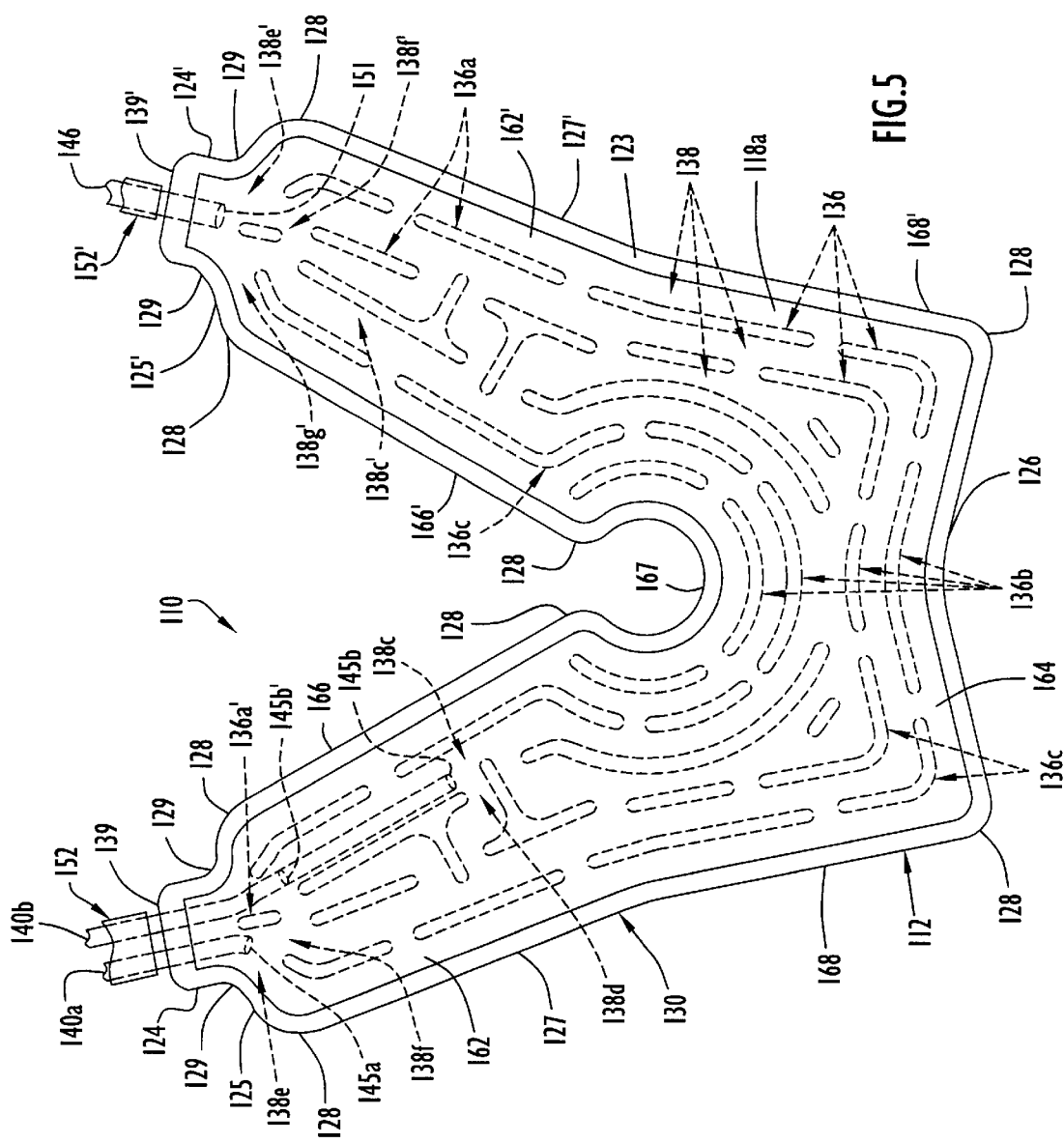
FIG. 5 is a broken, plan view of a modification of a therapeutic heat transfer pad according to the present invention.

A modified therapeutic heat transfer pad according to the present invention is illustrated at 110 in FIG. 5, the therapeutic heat transfer pad 110 being particularly suited for use on the fetlock area of a horse's leg. The heat transfer pad 110 is similar to the heat transfer pad 10 except that body portion 123 of pad assembly 112 of heat transfer pad 110 has a configuration defined by a pair of outwardly angled wing sections 162 and 162' connected to one another by a base section 164. The pad assembly 112 is constructed in the same manner as pad assembly 12 and includes outer sheet 118a connected or sealed to an inner sheet at edge seal 130 to define a fluid receiving cavity and at inner seals 136 to define fluid passages 138 as explained above. Wing sections 162 and 162' are symmetrical with base section 164 and extend outwardly therefrom at the same angle but in opposite directions. The wing sections 162 and 162' have lower ends, respectively, merging with the base section 164 and have upper ends, respectively, with neck portions 124 and 124', respectively, extending therefrom.

The wing sections 162 and 162' have straight outer sides or edges 127 and 127', respectively, and straight inner sides or edges 166 and 166', respectively. Each wing section has a width between its outer and inner sides, and each wing section is of gradually increasing width from the upper end to the lower end thereof. Inner sides 166 and 166' are connected to one another by an arcuate or partial circular upper side or edge 167 of base section 164, the inner sides 166 and 166' being connected to side 167 at rounded outside corners 128. Upper side 167 is centrally disposed between wing sections 162 and 162', which are symmetrical to upper side 167. Base section 164 also has straight outer sides or edges 168 and 168' merging with outer sides 127 and 127', respectively, and a gently curved lower side or edge 126 connected to outer sides 168 and 168' at rounded outside corners 128. The outer sides 168 and 168' are angularly joined to outer sides 127 and 127', respectively, and extend angularly outwardly from lower side 126 at the same angle but in opposite directions. The lower side 126 has a point of maximum curvature in line with the center of upper side 167.

The inner seals 136 include a plurality of straight inner seals 136a, a plurality of curved inner seals 136b and a plurality of angular inner seals 136c arranged in a manner to facilitate fluid flow and distribution in pad assembly 112. Some of the curved inner seals 136b follow the curvature of upper side 167 while other of the curved inner seals follow the curvature of lower side 126. Some of the angular inner seals 136c follow the bend or angle of corners 128 while other of the angular inner seals follow the angle formed by outer sides 127 and 127' with outer sides 168 and 168', respectively. The seals 126 are arranged symmetrically in pad assembly 112.

Neck portions 124 and 124' extend from the upper ends of wing sections 162 and 162', respectively, and, in particular, from upper sides or edges 125 and 125' of leg sections 162 and 162', respectively. The upper sides 125 and 125' are connected to the outer sides 127 and 127', respectively, at rounded outside corners 128, and the neck portions 124 and 124' are connected to the upper sides 125 and 125', respectively, at curved inside corners 129. Neck portion 124 has an outer end 139 through which inlet tubes 140a and 140b pass to enter into the fluid receiving cavity at a common entry point or location as described above for heat transfer pad 10. Inlet tube 140a has an open end 145a disposed within the fluid receiving cavity, and, in particular, the body portion 123, and inlet tube 140b has an open end 145b disposed in the cavity further interiorly of open end 145a. The length portion of inlet tube 140a disposed within the pad assembly 112 follows a partly straight and partly curved path such that the open end 145a curves toward and communicates directly with fluid passages 138e and 138f. The length portion of inlet tube 140b disposed within the pad assembly 112 follows a bent or angled path such that the open end 145b communicates directly with fluid passages 138c and 138d at a location in pad assembly 112 further interiorly of fluid passages 138e and 138f. The open end 145b' represents an alternative location for the open end of inlet tube 140b. The inlet tubes 140a and 140b are disposed on opposite sides of an inner seal 136a', and the location of open ends 145a and 145b facilitates the distribution of heat transfer fluid in pad assembly 112 as it is supplied to the fluid receiving cavity. A sheath 152 is disposed around the length portions of tubes 140a and 140b extending externally from the pad assembly 112, the sheath 152 extending from the outer edge 139 of neck portion 124 to the inlet coupling (not shown).

Neck portion 124' extends from the upper end of wing section 162' and has an outer end 139' through which outlet tube 146 passes to enter the fluid receiving cavity. Accordingly, the outlet tube enters the pad assembly at an entry point or location different from the common entry point or location for the inlet tubes. Outlet tube 146 has an open end 151 disposed in the fluid receiving cavity in direct communication with fluid passages 138c', 138e', 138f' and 138g'. A sheath 152' is disposed around the length portion of outlet tube 146 extending externally from the pad assembly 112, the sheath 152' extending from the outer edge 139' of neck portion 124' to the outlet coupling (not shown).

Use of therapeutic heat transfer pad 110 is similar to that described above for therapeutic heat transfer pad 10. The heat transfer pad 110 is applied to a body part or area to be treated and, in particular, the heat transfer pad 110 is applied to the fetlock area of a horse's leg with outer sides 127 and 168 in overlapping arrangement with outer sides 127' and 168' and inner side 166 in overlapping arrangement with inner side 166' such that the arcuate upper side 167 extends continuously around or encircles the fetlock of the horse's leg. Accordingly, when the outer and inner sides overlap or are in abutment, the upper side 167 forms a complete or continuous arcuate side or edge circumscribing a recess or opening for receiving a body protrusion, such as the fetlock, therein. In this manner, the pad assembly 112 can closely accommodate or receive fetlocks of various sizes while maximizing the area of the horse's leg to which heat or cold therapy is applied.

Figure 6:
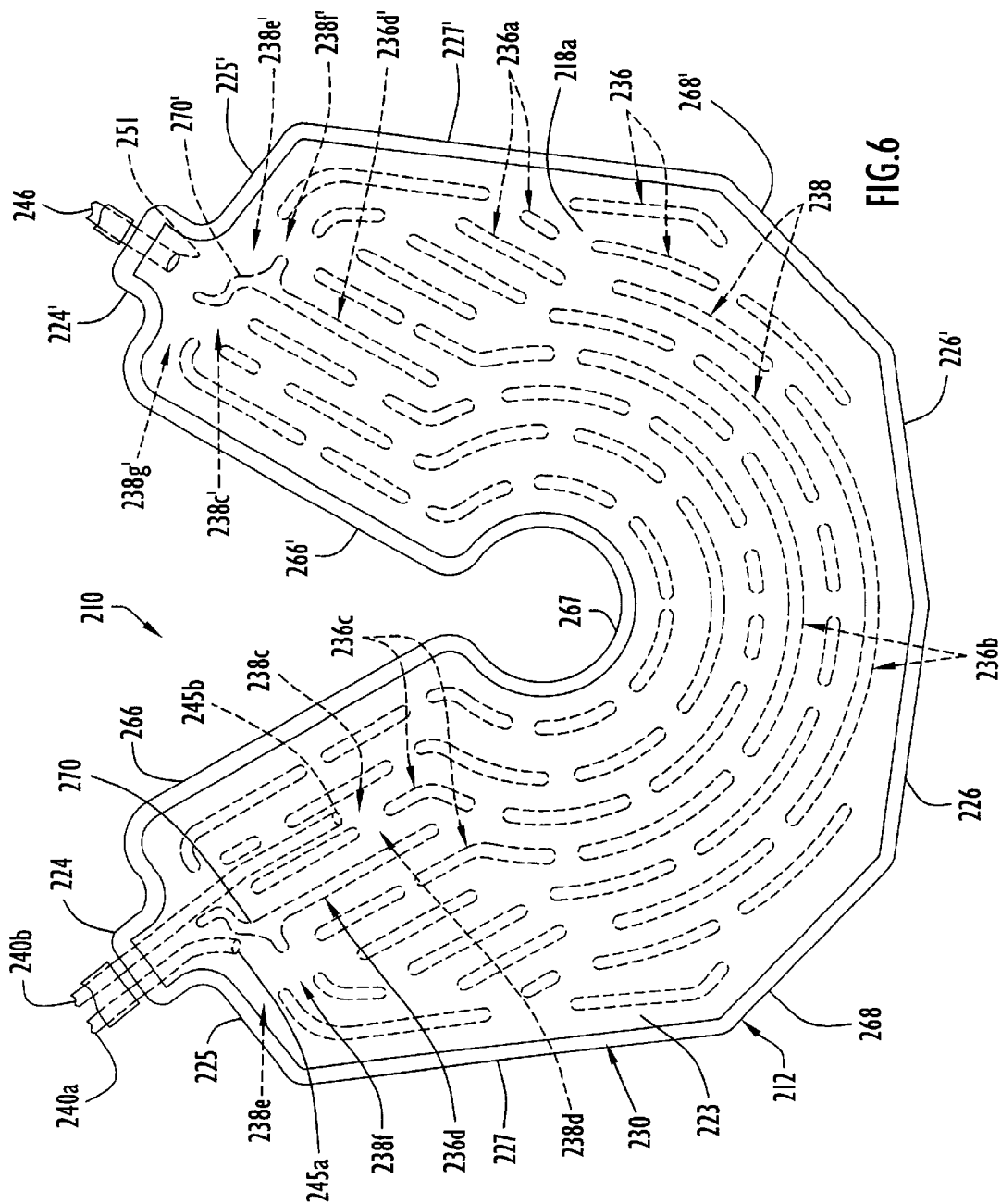
FIG. 6 is a broken, plan view of another modification of a therapeutic heat transfer pad according to the present invention.

Another modification of a therapeutic heat transfer pad according to the present invention is illustrated at 210 in FIG. 6, the heat transfer pad 210 being particularly suitable for use on the hock area of a horse's leg. The pad assembly 212 for heat transfer pad 210, which is similar to heat transfer pad 110, is constructed in the same manner as pad assembly 12 and includes outer sheet 218a joined to an inner sheet at edge seal 230, and inner seals 236 such that a fluid receiving cavity having a plurality of interconnected fluid passages 238 is defined in the pad assembly 212. The body portion 223 of pad assembly 212 has a configuration defined by straight inner sides or edges 266 and 266' connected to one another by an arcuate upper side or edge 267, a pair of straight outer sides or edges 227 and 227' extending from upper sides or edges 225 and 225', respectively, a pair of straight lower sides or edges 226 and 226' and a pair of straight outer sides or edges 268 and 268' connected between sides 227 and 226 and sides 227' and 226', respectively. Upper sides 225 and 225' are joined to outer sides 227 and 227', respectively, and to inner sides 266 and 266', respectively, by rounded outside corners. Neck portions 224 and 224' extend in a perpendicular direction from upper sides 225 and 225', respectively. The body portion 223 is symmetrical around upper side 267. The sides 227 and 227' are the same length and are joined to sides 268 and 268', respectively, at rounded outside corners. The sides 268 and 268' are the same length and are shorter than sides 227 and 227'. The sides 226 and 226', which are the same length as sides 268 and 268', meet one another at an outside corner and are joined to sides 268 and 268', respectively, at other outside corners. The outside corner at which sides 226 and 226'meet is in line with the center of upper side 267. The inner seals 236 include a plurality of straight inner seals 236a, a plurality of curved inner seals 236b, a plurality of angular inner seals 236c and a pair of inner seals 236d and 236d' each having a straight portion and a stepped portion connected to the straight portion, the seals 236 being arranged symmetrically in pad assembly 212. The inlet tubes 240a and 240b, which extend into the fluid receiving cavity via the neck portion 224, have their open ends 245a and 245b, respectively, disposed on opposite sides of the stepped portion 270 of the inner seal 236d. The open end 245a of inlet tube 240a is disposed over or above a sloping shoulder of the stepped portion 270 and is in direct fluid communication with fluid passages 238e and 238f. Fluid discharged from the open end 245a of inlet tube 240a will flow downwardly along the shoulder of stepped portion 270, as assisted by gravity, and will be distributed to fluid passages 238e and 238f. The open end 245b of inlet tube 240b is disposed in the fluid receiving cavity further interiorly of the open end 245a and is in direct communication with fluid passages 238c and 238d on the opposite side of inner seal 236d. The outlet tube 246 extends into the fluid receiving cavity via the neck portion 224'. The open end 251 of outlet tube 246 is disposed over or above the sloping shoulder of stepped portion 270' of the inner seal 236d' and is in direct communication with fluid passages 238c', 238e', 238f' and 238g'. The sloping shoulder of the stepped portion 270' of the inner seal 236d' facilitates removal of fluid from the fluid receiving cavity in that fluid is directed by the stepped portion to the open end 251.

The therapeutic heat transfer pad 210 is used in a manner similar to that described for heat transfer pads 10 and 110. In particular, the heat transfer pad 210 is positioned around the hock area of the leg of a horse so that the inner and outer sides are in overlapping arrangement as described for pad 210 such that the hock joint of the horse is disposed in the opening or recess formed by upper side 267. In this manner, the horse's leg will be encircled or surrounded by the pad assembly 212 and the hock joint of the horse will be circumscribed by the arcuate side 267.

Figure 7:
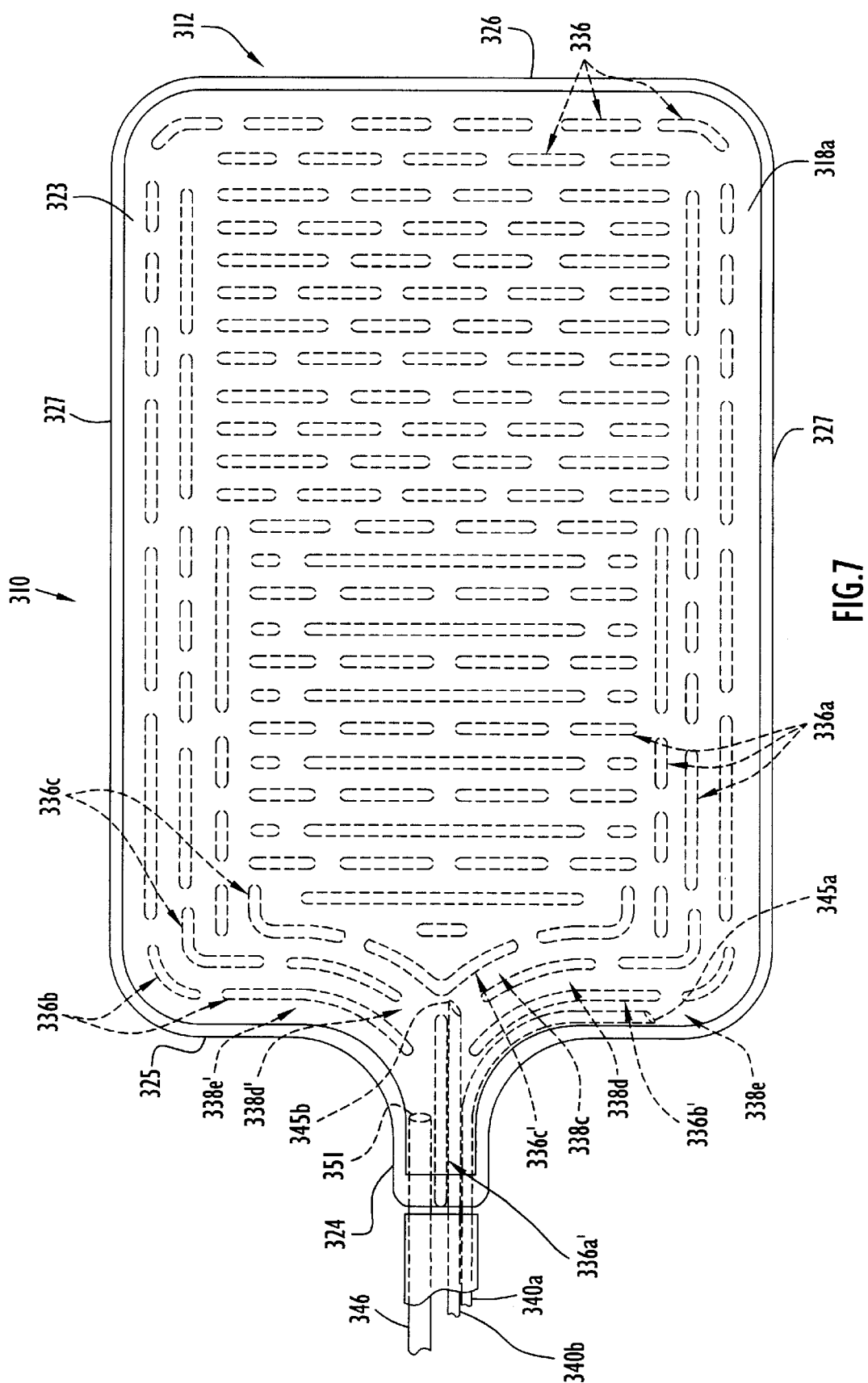
FIG. 7 is a broken, plan view of a further modification of a therapeutic heat transfer pad according to the present invention.

Another modification of a therapeutic heat transfer pad according to the present invention is illustrated at 310 in FIG. 7. The heat transfer pad 310 is similar to heat transfer pad 10, except that body portion 323 of pad assembly 312 for heat transfer pad 310 has a rectangular configuration that is particularly advantageous for use on an area of the back of a horse. Pad assembly 312 includes outer sheet 318a connected to an inner sheet along perimetrical edge seal 330 and along inner seals 336. The body portion 323 of pad assembly 312 is defined by parallel straight sides or edges 327 and parallel straight sides or edges 325 and 326 connected to sides 327, respectively, at rounded outside corners. Neck portion 324 of pad assembly 312 extends in a perpendicular direction from side 325 and is axially aligned with a central longitudinal axis of the pad assembly 312, the neck portion 324 being connected to side 325 by curved inside corners. The inner seals 336 include a straight inner seal 336a' extending centrally along neck portion 324 and into body portion 323, a plurality of additional straight inner seals 336a, some of which are disposed parallel to the central longitudinal axis and some of which are disposed perpendicular to the central longitudinal axis, a plurality of curved inner seals 336b that follow or substantially follow the curvature of the outside and inside corners and a plurality of angular inner seals 336c that follow or substantially follow the bend or curve of the corners. One of the angular inner seals, i.e. inner seal 336c', has a V shape including a pair of curved arms joined at a junction and extending angularly outwardly from one another in the direction of sides 327, respectively, the junction being longitudinally aligned with seal 336a' but spaced therefrom. Inlet tubes 340a and 340b are disposed on one side of inner seal 336a', and outlet tube 346 is disposed on the opposite side of inner seal 336a' as described for heat transfer pad 10. The length portion of inlet tube 340b disposed in the pad assembly 312 follows a straight path while the length portion of inlet tube 340a disposed in the pad assembly 312 follows a curved path. The inlet tube 340b extends along seal 336a' parallel therewith, and the open end 345b of inlet tube 340b is in direct communication with fluid passages 338c and 338d. The inlet tube 340a follows the curvature of an inside corner and is disposed between edge seal 330 and a curved seal 336b'. There may be a small gap between tube 340a and seals 330 and 336b' allowing fluid to flow therebetween. The open end 345a of inlet tube 340a communicates with fluid passages 338d and 338e. The open end 351 of the outlet tube 346 is in communication with fluid passages 338d' and 338e'.

When used for heat and/or cold therapy, the heat transfer pad 310 does not have to be wrapped around a body part or area but, rather, may merely be placed upon a body part or area to be treated such that the pad assembly 312 is supported by such body part or area. For example, the pad assembly 312 may merely be placed upon or draped over the back of a horse. Of course, the pad assembly 312 can be secured to a body part or area with a wrap, tape or bandage as previously described. Fluid supplied to the pad assembly via the inlet tubes 340a and 340b enters different ones of the fluid passages due to the spacing between open ends 345a and 345b. In addition, fluid discharged from each of the open ends 345a and 345b is discharged into more than one fluid passage. The flow of fluid from the open ends 345a and 345b is facilitated and guided by the curvature of the inner seals. The curvature of the inner seals in the vicinity of the open end 351 of outlet tube 346 facilitates and guides fluid flow into the open end 351 for removal of the fluid from the pad assembly.

Figure 8:
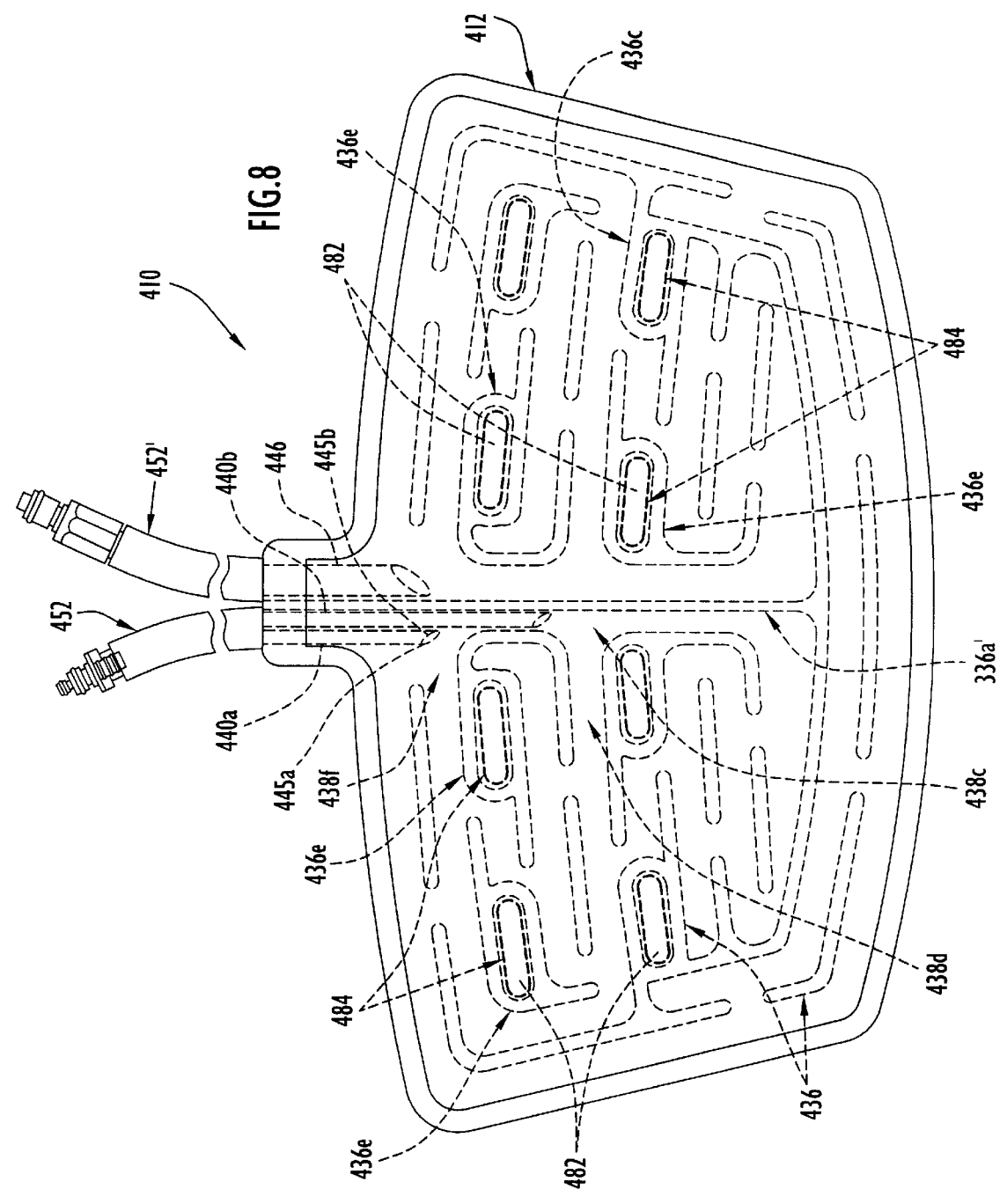

Another modification of a therapeutic heat transfer pad according to the present invention is illustrated at 410 in FIG. 8. The heat transfer pad 410 is similar to the heat transfer pad 10 except that the heat transfer pad 410 includes a plurality of magnets 482 for magnetic therapy of the body part or area to be treated. The heat transfer pad 410 differs from heat transfer pad 10 in that some of the inner seals 436 of heat transfer pad 410 form pockets 484 in pad assembly 412. As shown in FIG. 8, inner seals 436e each circumscribe a pocket 484 between the outer sheet and the inner sheet of the pad assembly 412. Magnets 482 are disposed in the pockets 484 and are sealed or isolated by seals 336e from fluid within the fluid receiving cavity. The magnets 482 may include any type of magnet, including unipolar and bipolar magnets, capable of providing a magnetic field for medicinal purposes, and any number of magnets 482 may be provided in the pad assembly 412 in accordance with the therapeutic effect desired to be obtained. The magnetic therapy provided by magnets 482 provides various beneficial effects in the body part or area being treated, including promoting healing processes, stimulating blood circulation, improving oxygen consumption by cells and reducing inflammation, for example. The therapeutic heat transfer pad 410 allows two forms of therapy, i.e., heat or cold therapy and magnetic therapy, to be conducted with a single device.

The heat transfer pad 410 also differs from heat transfer pad 10 in that the length portion of inlet tube 440a that is disposed in the pad assembly 412 follows a straight path. The length portion of inlet tube 440a disposed in pad assembly 412 is parallel to the length portion of inlet tube 440b that is disposed in pad assembly 412. The distance that the inlet tube 440a extends into the pad assembly 412 is less than the distance that the inlet tube 440b extends into the pad assembly 412. The open end 445b of inlet tube 440b is in direct communication with fluid passages 438d and 438c. The open end 445a of inlet tube 440a is in direct communication with fluid passages 438c and 438f, the open end 445a communicating with fluid passage 438c at a location different than the location at which open end 445b communicates with fluid passage 438c. The heat transfer pad 410 has two sheaths 452 and 452', the sheath 452 being disposed around inlet tubes 440a and 440b and the sheath 452' being disposed around the outlet tube 446.

Another modification of a therapeutic heat transfer pad according to the present invention is illustrated at 510 in FIG. 9. The heat transfer pad 510 is similar to heat transfer pad 10 except that panel 522 for heat transfer pad 510 is made of magnetic material. As shown in FIG. 9, pad assembly 512 includes outer sheets 518a and 518b, inner sheet 520 disposed between outer sheets 518a and 518b and panel 522 disposed between inner sheet 520 and outer sheet 518b. Panel 522 is a magnet 582 of uniform thickness and having a perimetrical or peripheral configuration to be disposed within or inside of edge seal 530.

The therapeutic heat transfer pads according to the present invention provide for enhanced fluid flow and distribution within the pads, reduce bending or sagging of the pads for enhanced ease of use, deter obstruction or blockage of the fluid passages and inhibit kinking or twisting of the inlet and/or outlet tubes. A heat transfer fluid at a desired temperature enters the pads at different, spaced locations within the pads. The pads can have various configurations in accordance with the body parts or areas to be treated and the manner in which the pads are to be applied to such body parts or areas. Various arrangements of inner seals can be provided in the pads to define fluid passages within the pads arranged and oriented to facilitate fluid flow and distribution therein. The heat transfer pads can be provided with an insulated panel incorporated therein to minimize heat transfer to and from the fluid within the pads and/or to serve as padding. The pads can be provided with one or more magnets for effecting magnetic therapy, and the magnets can be disposed within pockets formed in the pads. The heat transfer pads are particularly useful for therapeutic treatment of race horses and, in particular, on the cannons/pasterns, fetlocks, hocks and backs of race horses.

Inasmuch as the subject invention is subject to many variations, modifications and changes in detail, it is intended that all subject matter discussed above or shown in the accompanying drawings be interpreted as illustrative only and not be taken in a limiting sense.

What is claimed is:

1. A therapeutic heat transfer pad for application to a body area comprising
   a pad assembly including two sheets of impervious material, said sheets having perimeters, respectively, an edge seal connecting said sheets to one another continuously along said perimeters to form a fluid receiving cavity between said sheets, a plurality of inner seals disposed interiorly of said edge seal at which said sheets are connected to one another to form a plurality of interconnected fluid passages in said pad assembly;
   first and second fluid inlet tubes extending into said fluid receiving cavity from externally of said pad assembly for introduction of a heat transfer fluid into said fluid passages, said inlet tubes entering said fluid receiving cavity at the same location and terminating at open ends, respectively, disposed within said fluid receiving cavity and through which the heat transfer fluid is introduced in said fluid passages, one of said inlet tubes extending into said fluid receiving cavity a greater distance than the other such that said open ends are in communication with different ones of said fluid passages; and
   an outlet tube extending into said fluid receiving cavity from externally of said pad assembly and terminating at an open end disposed within said fluid receiving cavity for removing the heat transfer fluid therefrom.

2. A therapeutic heat transfer pad as recited in claim 1 wherein said inlet tubes are disposed alongside one another at said location.

3. A therapeutic heat transfer pad as recited in claim 1 wherein each of said open ends of said inlet tubes communicates directly with more than one of said fluid passages.

4. A therapeutic heat transfer pad as recited in claim 1 wherein said outlet tube enters said fluid receiving cavity at said location.

5. A therapeutic heat transfer pad as recited in claim 1 wherein said open end of said outlet tube is in communication with a further one of said fluid passages.

6. A therapeutic heat transfer pad as recited in claim 1 wherein said inlet tubes include first length portions, respectively, disposed in said pad assembly and second length portions, respectively, extending externally of said pad assembly, one of said first length portions being longer than the other.

7. A therapeutic heat transfer pad as recited in claim 6 wherein one of said first length portions follows a straight path in said pad assembly and the other of said first length portions follows a non-straight path in said pad assembly.

8. A therapeutic heat transfer pad as recited in claim 6 and further including a sheath disposed around said second length portions.

9. A therapeutic heat transfer pad as recited in claim 8 wherein said outlet tube includes a first length portion disposed in said pad assembly and a second length portion extending externally of said pad assembly and said sheath is disposed around said second length portion of said outlet tube.

10. A therapeutic heat transfer pad for application to a body area comprising
    a pad assembly including two sheets of impervious material having perimeters, respectively, an edge seal connecting said sheets to one another continuously along said perimeters to form a fluid receiving cavity therebetween, a plurality of inner seals, disposed interiorly of said edge seal, at which said sheets are connected to one another to form a plurality of interconnected fluid passages in said fluid receiving cavity, said pad assembly having a perimetrical configuration defined by a body portion and a neck portion extending from said body portion;
    a fluid inlet member passing between said sheets to enter said fluid receiving cavity from externally of said pad assembly for introducing a heat transfer fluid into said fluid passages, said fluid inlet member entering said pad assembly at said neck portion and extending interiorly beyond said neck portion into said body portion, said fluid inlet member including first and second inlet tubes terminating at open ends, respectively, disposed in said fluid receiving cavity and through which the heat transfer fluid is introduced in said fluid passages, said open ends being disposed in said body portion at spaced locations within said fluid receiving cavity so as to communicate with different ones of said fluid passages; and
    an outlet tube passing between said sheets to enter said fluid receiving cavity from externally of said pad assembly and terminating at an open end disposed in said fluid receiving cavity for removing the heat transfer fluid therefrom.

11. A therapeutic heat transfer pad as recited in claim 10 wherein said perimetrical configuration is defined by said body portion, said neck portion and another neck portion extending from said body portion, said outlet tube entering said pad assembly at said another neck portion.

12. A therapeutic heat transfer pad as recited in claim 10 and further including an additional sheet of impervious material disposed on top of one of said sheets, said additional sheet having a perimeter continuously secured by said edge seal to said perimeter of said one of said sheets to define a space between said additional sheet and said one of said sheets, and a panel disposed in said space.

13. A therapeutic heat transfer pad as recited in claim 12 wherein said panel is made of soft, insulative material.

14. A therapeutic heat transfer pad as recited in claim 12 wherein said panel is made of magnetic material.

15. A therapeutic heat transfer pad as recited in claim 10 wherein said inner seals include a plurality of straight inner seals, a plurality of curved inner seals and a plurality of angular inner seals.

16. A therapeutic heat transfer pad as recited in claim 10 wherein said body portion is defined by outer sides adapted to meet one another when said pad assembly is applied to a body area such that said pad assembly is positionable to encircle a body limb.

17. A therapeutic heat transfer pad as recited in claim 10 wherein said body portion is defined by outer sides adapted to meet one another and inner sides adapted to meet one another when said pad assembly is applied to a body area, said body portion circumscribing an opening when said outer sides meet one another and said inner sides meet one another, said opening being adapted to receive a body protrusion therein.

* * * * *